United States Patent
Peltola et al.

(10) Patent No.: US 12,121,747 B2
(45) Date of Patent: Oct. 22, 2024

(54) ARTIFICIAL INTELLIGENCE MODELING FOR RADIATION THERAPY DOSE DISTRIBUTION ANALYSIS

(71) Applicant: Siemens Healthineers International AG, Steinhausen (CH)

(72) Inventors: Jarkko Peltola, Helsink (FI); Marko Rusanen, Helsinki (FI); Ville Pietila, Helsinki (FI)

(73) Assignee: SIEMENS HEALTHINEERS INTERNATIONAL AG, Steinhausen (CH)

(*) Notice: Subject to any disclaimer, the term of this patent is extended or adjusted under 35 U.S.C. 154(b) by 765 days.

(21) Appl. No.: 17/208,781

(22) Filed: Mar. 22, 2021

(65) Prior Publication Data

US 2022/0296924 A1  Sep. 22, 2022

(51) Int. Cl.
*G16H 20/40* (2018.01)
*A61N 5/10* (2006.01)
*G06N 20/00* (2019.01)
*G16H 30/40* (2018.01)

(52) U.S. Cl.
CPC .......... *A61N 5/1031* (2013.01); *A61N 5/1038* (2013.01); *G06N 20/00* (2019.01); *G16H 20/40* (2018.01); *G16H 30/40* (2018.01)

(58) Field of Classification Search
CPC .... A61N 5/1031; A61N 5/1038; G16H 20/40; G16H 30/40; G06N 20/00
See application file for complete search history.

(56) References Cited

U.S. PATENT DOCUMENTS 11,850,445 B2 * 12/2023 Hibbard .............. A61N 5/1039
2016/0140300 A1    5/2016 Purdie et al.
2019/0333623 A1   10/2019 Hibbard

OTHER PUBLICATIONS

International Search Report and Written Opinion on PCT Appl. Ser. No Ser. No. PCT/EP2022/057059 dated Jul. 5, 2022 (13 pages).

* cited by examiner

*Primary Examiner* — David P Porta
*Assistant Examiner* — Fani Polyzos Boosalis
(74) *Attorney, Agent, or Firm* — FOLEY & LARDNER LLP

(57) ABSTRACT

Disclosed herein are methods and systems to optimize a radiation therapy treatment plan using dose distribution values predicted via a trained artificial intelligence model. A server trains the AI model using a training dataset comprising data associated with a plurality of previously implemented radiation therapy treatments on a plurality of previous patients and dose distributions associated with one or more organs of each previous patient. The server then executes the trained AI model to predict dose distribution for a patient. The server then displays a heat map illustrating the predicted values, transmits the predicted values to a plan optimizer to generate an optimized treatment plan for the patient, and/or transmits an alert when a treatment plan generated by a plan optimizer deviates from rules and thresholds indicated within the patient's plan objectives.

18 Claims, 7 Drawing Sheets

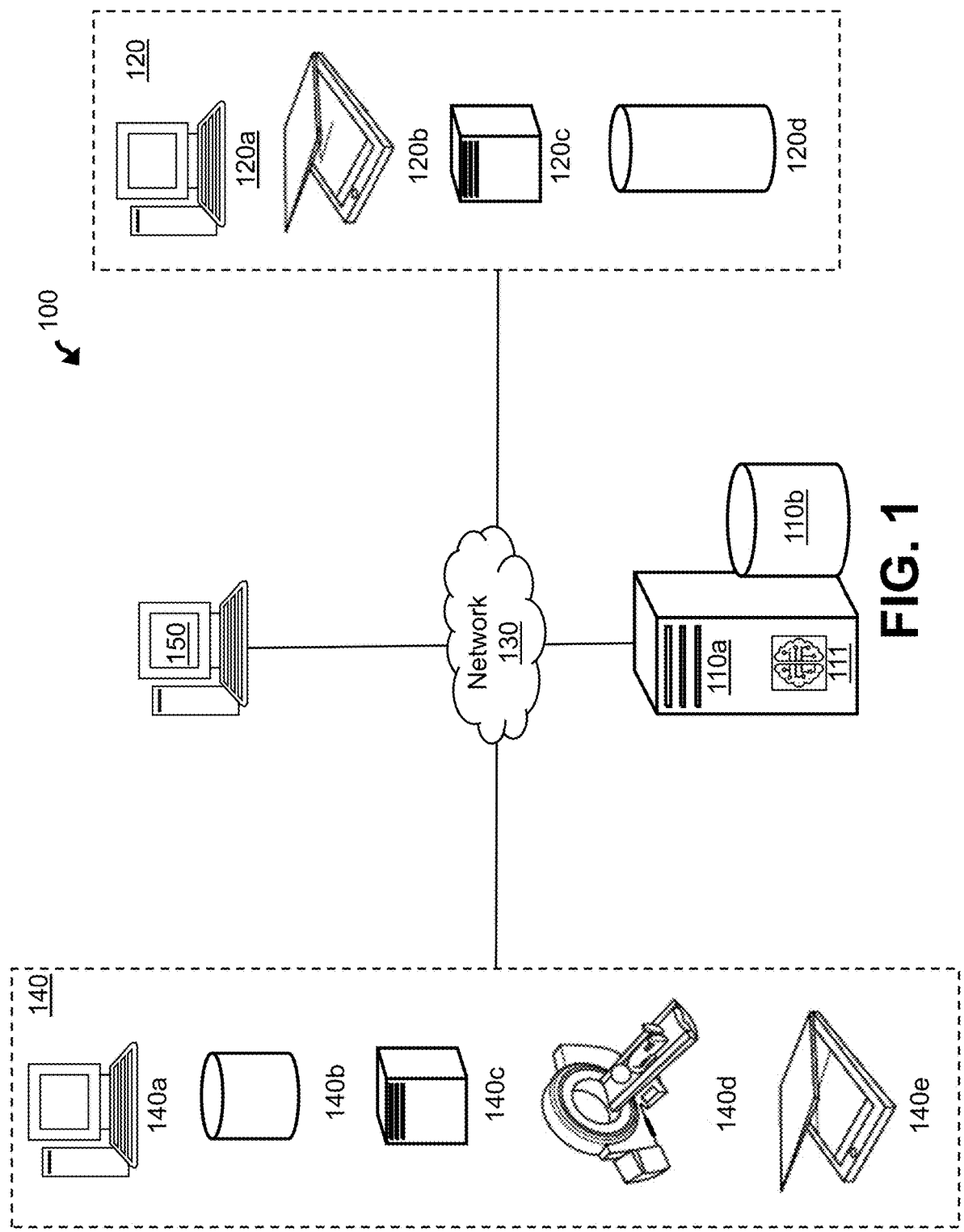

Executing an artificial intelligence model to identify a dose distribution value associated for an anatomical region of a new patient, the artificial intelligence model trained using a training dataset comprising data associated with a plurality of previously implemented radiation therapy treatments on a plurality of previous patients and dose distributions associated with one or more anatomical regions of each previous patient. 210

Displaying a heat map having a set of segments where each segment corresponds to a first coordinate and a second coordinate of the organ of the new patient, wherein a visual attribute of each segment corresponds to a calculated dose distribution value, wherein at least one segment corresponding to a hot spot exceeding a first threshold or a cold spot below a second threshold is visually distinct from other segments within the heat map. 220

FIG. 2

ARTIFICIAL INTELLIGENCE MODELING FOR RADIATION THERAPY DOSE DISTRIBUTION ANALYSIS

TECHNICAL FIELD

This application relates generally to using artificial intelligence modeling to predict, visualize, and optimize dose distributions and treatment plans for patient.

BACKGROUND

Radiotherapy (radiation-based therapy) is used as a cancer treatment to emit high doses of radiation that can kill cells or shrink a tumor. The target region of a patient's body that is intended to receive radiation (e.g., tumor) is referred to as the planning target volume (PTV). The goal is to deliver enough radiation to the PTV to kill the cancerous cells during a radiotherapy treatment (also referred to herein as a treatment plan or radiation therapy treatment). However, other organs or anatomical regions that are adjacent to, or surrounding, the PTV can be in the path of radiation beams and can receive enough radiation to damage or harm such organs or anatomical regions. These organs or anatomical regions are referred to as organs at risk (OARs). Usually, a physician or a radiologist identifies both the PTV and the OARs prior to radiotherapy using, for example, computed tomography (CT) images, magnetic resonance imaging (MM) images, positron emission tomography (PET) images, images obtained via some other imaging modality, or a combination thereof. For instance, the physician or the radiologist may manually mark the PTV and/or the OARs on the medical images of the patient.

Using the medical images of the patient as well as the identified PTV and the OARs, a team of medical professionals (e.g., physicians, radiologists, oncologists, radiology technicians, other medical personnel or a combination thereof) determines the radiation parameters to be used during the radiotherapy treatment. These radiation parameters include, for example, the type, the angle, the radiation intensity and/or the shape of each radiation beam. In determining these parameters, the medical professional attempts to achieve a radiation dose distribution to deliver to the patient that meets predefined criteria (also referred to herein as the plan objectives). Such criteria usually include predefined radiation dose thresholds or ranges for the PTV and the OARs.

To optimize the radiation parameters in a way to meet the predefined criteria, a treatment planner usually runs a plurality of simulations with various radiation parameters and selects a final set of radiation parameters to be used based on the simulation results. However, this process is highly inefficient and undesirable. This process usually involves revising the radiation parameters after each simulation. Such an approach is time consuming, tedious, and may not provide optimal results, regardless of whether the radiation parameters are calculated using manual or computer-based solutions. Furthermore, this conventional approach heavily relies on the medical professional's subjective knowledge and understanding.

SUMMARY

For the aforementioned reasons, there is a desire for an automated end-to-end system that can adapt a computer model (e.g., an artificial intelligence model) to automatically simulate a patient's treatment plan and dose distribution and to optimize the patient's treatment plan in a manner that does not depend on a medical professional's subjective skills and understanding. There is a desire to generate an accurate prediction of dose distributions that can be used for guiding clinical plan optimization and to save calculation time.

In an embodiment, a method comprises executing, by a processor, an artificial intelligence model to identify a dose distribution value for an anatomical region of a patient, the artificial intelligence model trained using a training dataset comprising data associated with a plurality of previously implemented radiation therapy treatments on a plurality of previous patients and dose distributions associated with one or more organs of each previous patient; and displaying, by the processor, a heat map having a set of segments where each segment corresponds to a first coordinate and a second coordinate of the anatomical region of the patient, wherein a visual attribute of each segment corresponds to a calculated dose distribution value, wherein at least one segment corresponding to a first region exceeding a first threshold or a second region below a second threshold is visually distinct from other segments within the heat map.

In another embodiment, a computer system comprises a server comprising a processor and a non-transitory computer-readable medium containing instructions that when executed by the processor causes the processor to perform operations comprising: execute an artificial intelligence model to identify a dose distribution value for an anatomical region of a patient, the artificial intelligence model trained using a training dataset comprising data associated with a plurality of previously implemented radiation therapy treatments on a plurality of previous patients and dose distributions associated with one or more organs of each previous patient; and display a heat map having a set of segments where each segment corresponds to a first coordinate and a second coordinate of the anatomical region of the patient, wherein a visual attribute of each segment corresponds to a calculated dose distribution value, wherein at least one segment corresponding to a first region exceeding a first threshold or a second region below a second threshold is visually distinct from other segments within the heat map.

In another embodiment, a computer system comprises a processor in communication with an artificial intelligence model and an electronic device, the processor configured to: execute the artificial intelligence model to identify a dose distribution value for an anatomical region of a patient, the artificial intelligence model trained using a training dataset comprising data associated with a plurality of previously implemented radiation therapy treatments on a plurality of previous patients and dose distributions associated with one or more organs of each previous patient; and display, on the electronic device, a heat map having a set of segments where each segment corresponds to a first coordinate and a second coordinate of the anatomical region of the patient, wherein a visual attribute of each segment corresponds to a calculated dose distribution value, wherein at least one segment corresponding to a first region exceeding a first threshold or a second region below a second threshold is visually distinct from other segments within the heat map.

In another embodiment, a method comprises retrieving, by a processor, a radiation therapy treatment plan for a patient comprising a plan dose distribution value associated with the patient; executing, by the processor using the radiation therapy treatment plan, an artificial intelligence model to predict a predicted dose distribution value for an anatomical region of the patient based at least in part on the plan dose distribution, the artificial intelligence model trained using a training dataset comprising data associated with a plurality of previously implemented radiation therapy treatments on a plurality of previous patients and dose distributions associated with one or more organs of each previous patient; and transmitting, by the processor, a notification when the predicted dose distribution value exceeds a threshold.

In another embodiment, a computer system comprises a server comprising a processor and a non-transitory computer-readable medium containing instructions that when executed by the processor causes the processor to perform operations comprising: retrieve a radiation therapy treatment plan for a patient comprising a plan dose distribution value associated with the patient; execute, using the radiation therapy treatment plan, an artificial intelligence model to predict a predicted dose distribution value for an anatomical region of the patient based at least in part on the plan dose distribution value, the artificial intelligence model trained using a training dataset comprising data associated with a plurality of previously implemented radiation therapy treatments on a plurality of previous patients and dose distributions associated with one or more organs of each previous patient; and transmit a notification when the predicted dose distribution value exceeds a threshold.

In another embodiment, a computer system comprises a processor in communication with an artificial intelligence model and an electronic device, the processor configured to: retrieve a radiation therapy treatment plan for a patient; execute comprising a plan dose distribution value associated with the patient, using the radiation therapy treatment plan, the artificial intelligence model to predict a predicted dose distribution value for an anatomical region of the patient, the artificial intelligence model trained using a training dataset comprising data associated with a plurality of previously implemented radiation therapy treatments on a plurality of previous patients and dose distributions associated with one or more organs of each previous patient; and transmit a notification, to the electronic device, when the predicted dose distribution value exceeds a threshold.

BRIEF DESCRIPTION OF THE DRAWINGS

Non-limiting embodiments of the present disclosure are described by way of example with reference to the accompanying figures, which are schematic and are not intended to be drawn to scale. Unless indicated as representing the background art, the figures represent aspects of the disclosure.

FIG. 1 illustrates components of an automated dose distribution analysis system, according to an embodiment.

FIG. 2 illustrates a flow diagram of a process executed in an automated dose distribution analysis system, according to an embodiment.

DETAILED DESCRIPTION

Figure 3:
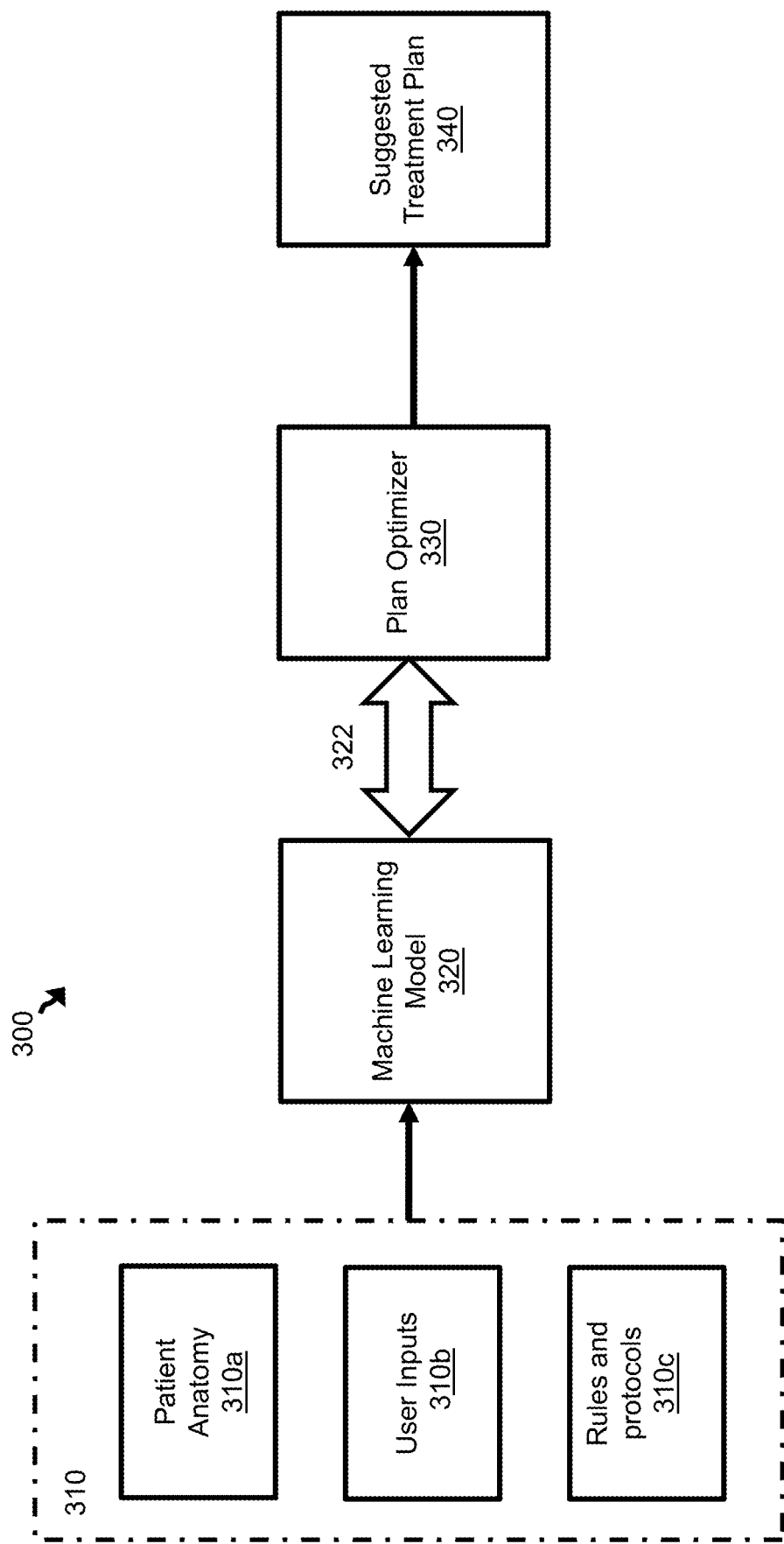
FIG. 3 illustrates a flow diagram of a process executed in an automated dose distribution analysis system, according to an embodiment.

Reference will now be made to the illustrative embodiments depicted in the drawings, and specific language will be used here to describe the same. It will nevertheless be understood that no limitation of the scope of the claims or this disclosure is thereby intended. Alterations and further modifications of the inventive features illustrated herein, and additional applications of the principles of the subject matter illustrated herein, which would occur to one skilled in the relevant art and having possession of this disclosure, are to be considered within the scope of the subject matter disclosed herein. Other embodiments may be used and/or other changes may be made without departing from the spirit or scope of the present disclosure. The illustrative embodiments described in the detailed description are not meant to be limiting of the subject matter presented.

Clinics may utilize software solutions for radiation therapy treatment planning (RTTP) and to optimize a treatment plan for patients. These software solutions (referred to herein as a plan optimizer or plan optimizer application) may analyze patient data, clinical goals, and a multitude of other factors to generate a customized treatment plan for a patient. The plan optimizer may be a set of computer-readable instructions stored on a non-transitory computer medium and configured to be executed by a processor to carry out this functionality. The customized treatment plan may also consider how dosages are distributed among the patient's organs to ensure radiation is appropriately applied to PTV without compromising OARs.

By implementing the systems and methods described herein, a clinic may augment the above-describe process by utilizing artificial intelligence (AI) models that can predict dose distribution among the patient's organs or for a particular anatomical region of the patient. AI models may be used in automatic organ and tumor segmentation. AI models may also provide decision support by, for example, suggesting that a treatment plan (generated by the plan optimizer) may result in inappropriate dose distribution. As will be described below, a clinic may utilize the methods and systems described herein in conjunction with an existing plan optimizer to improve the patient's treatment plan. AI models can be trained based on historical data and/or trained using granular data (e.g., based on a specific patient), such that the AI model's predictions are specific to a particular patient. Therefore, when used in conjunction with plan optimizers, the AI models can improve the treatment plan's accuracy.

Additionally or alternatively, the methods and systems described herein can be used to provide an independent audit/evaluation of treatment plans generated by a plan optimizer. For instance, an AI model can be executed to determine whether a treatment plan would result in inappropriate dose distribution. Additionally or alternatively, the methods and systems described herein can be used to simulate and visualize dose distribution for a patient based on a suggested treatment plan. Using the methods and systems described herein, a server (e.g., a central server or a computer associated with a specific clinic) may calibrate treatment plans using specially trained AI models.

By implementing the systems and methods described herein, a clinic may avoid the costs and processing resources that are typically required to generate treatment plans. Moreover, the solution may allow for cross-clinical comparisons for plan optimizer and the model's performance in terms of reliability.

As will be described below, a server (referred to herein as the analytics server) can train an AI model (e.g., neural network or other machine-learning models) using historical treatment data and/or patient data from the patient's previous treatments. In a non-limiting example, the analytics server may transfer, or a processor of a clinic may otherwise access, the trained AI model to a processor associated with the clinic for calibration and/or evaluation of treatment plans. FIG. 1 is an example of components of a system in which the analytics server operates. Various other system architectures that may include more or fewer features may utilize the methods described herein to achieve the results and outputs described herein. Therefore, the system depicted in FIG. 1 is a non-limiting example.

FIG. 1 illustrates components of an automated dose distribution analysis system 100. The system 100 may include an analytics server 110a, system database 110b, AI models 111, electronic data sources 120a-d (collectively electronic data sources 120), end-user devices 140a-e (collectively end-user devices 140), and an administrator computing device 150. Various features depicted in FIG. 1 may belong to a radiotherapy clinic at which patients may receive radiotherapy treatment, in some cases via one or more radiotherapy machines located within the clinic (e.g., radiotherapy machine 140d).

The above-mentioned components may be connected to each other through a network 130. Examples of the network 130 may include, but are not limited to, private or public LAN, WLAN, MAN, WAN, and the Internet. The network 130 may include wired and/or wireless communications according to one or more standards and/or via one or more transport mediums. The communication over the network 130 may be performed in accordance with various communication protocols such as Transmission Control Protocol and Internet Protocol (TCP/IP), User Datagram Protocol (UDP), and IEEE communication protocols. In one example, the network 130 may include wireless communications according to Bluetooth specification sets or another standard or proprietary wireless communication protocol. In another example, the network 130 may also include communications over a cellular network, including, for example, a GSM (Global System for Mobile Communications), CDMA (Code Division Multiple Access), EDGE (Enhanced Data for Global Evolution) network.

The system 100 is not confined to the components described herein and may include additional or other components, not shown for brevity, which are to be considered within the scope of the embodiments described herein.

The analytics server 110a may generate and display an electronic platform configured to use various computer models 111 (including artificial intelligence and/or machine-learning models) to identify and display treatment attributes (e.g., RTTP that includes different radiation parameters). More specifically, the platform may display dose distribution data. The electronic platform may include graphical user interfaces (GUIs) displayed on each electronic data source 120, the end-user devices 140, and/or the administrator computing device 150. An example of the electronic platform generated and hosted by the analytics server 110a may be a web-based application or a website configured to be displayed on different electronic devices, such as mobile devices, tablets, personal computer, and the like. In a non-limiting example, a physician operating the physician device 120b may access the platform, input patient attributes or characteristics and other data, and further instruct the analytics server 110a to optimize the patient's treatment plan (e.g., dose distribution among the patient's organs). The analytics server 110a may utilize the methods and systems described herein to optimize dosage distribution and display the results on the end-user devices or adjust the configuration of one of end-user devices 140 (e.g., the radiotherapy machine 140d). The analytics server 110a may display the predicted dose distribution and/or radiation parameters on the physician device 120b itself as well.

Figure 5:
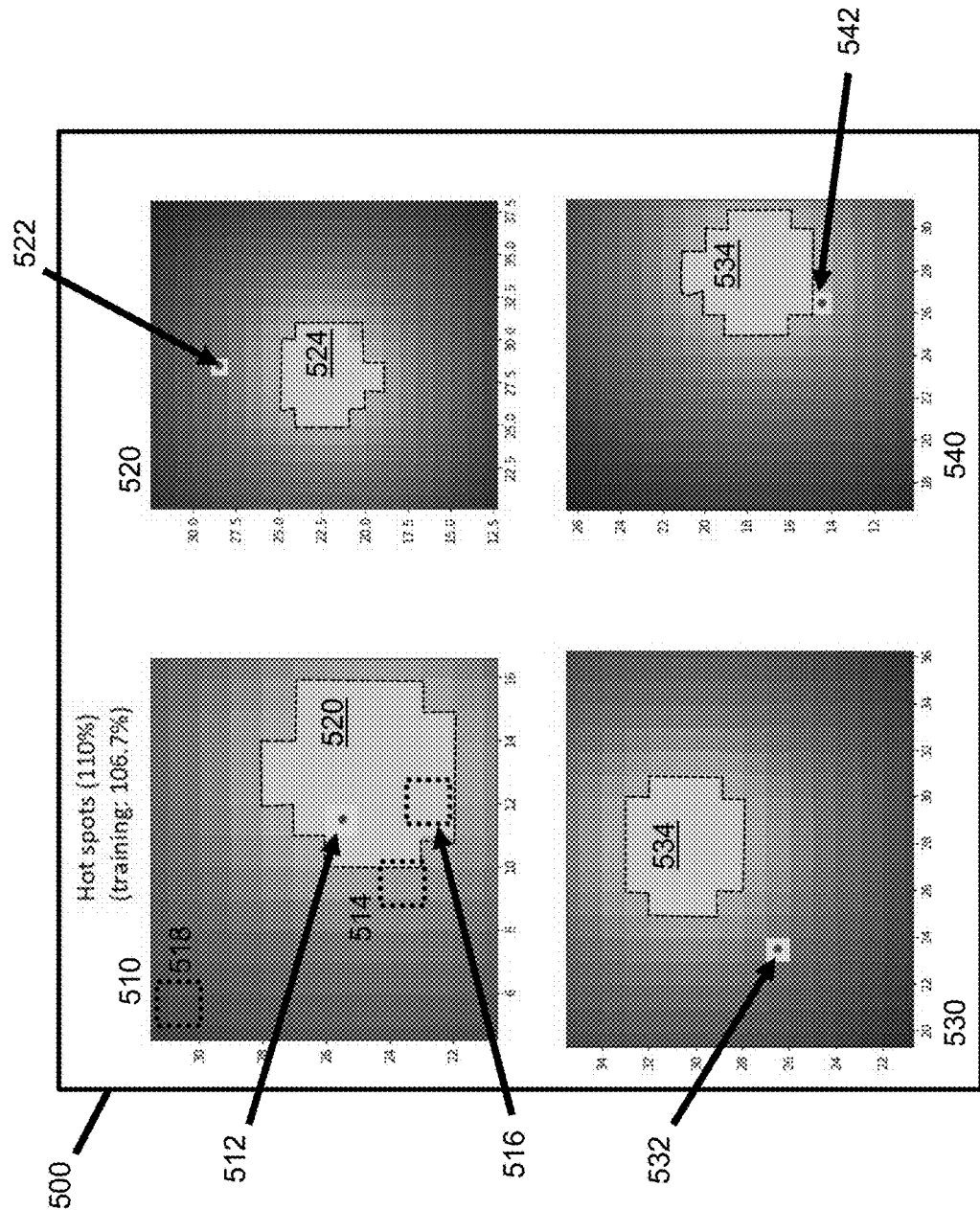
FIGS. 5-6 illustrate graphical user interfaces generated and displayed in an automated dose distribution analysis system, according to an embodiment.
Figure 6:
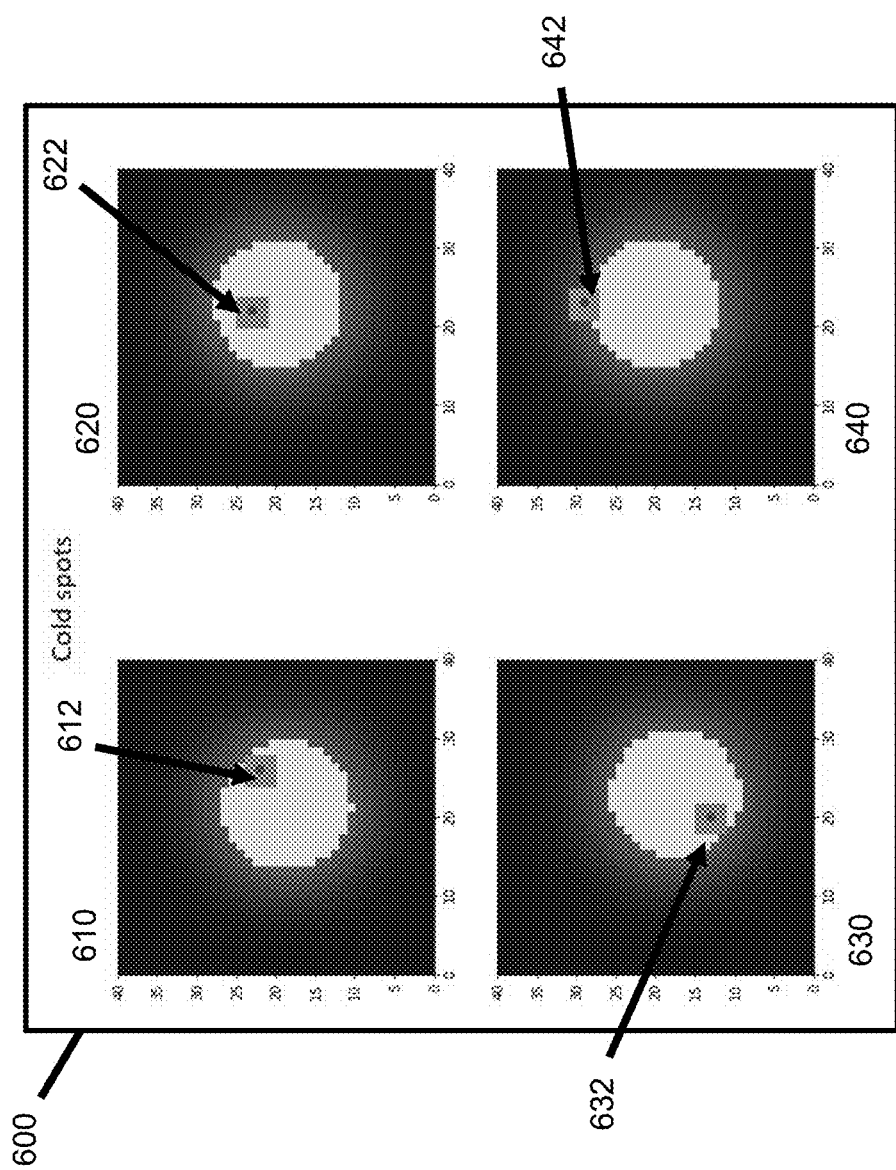

As described herein, radiation parameters may be or include any attributes related to treating patients at a radiotherapy clinic and/or using a radiotherapy machine. Radiation parameters may include, but are not limited to, different treatment modalities, field geometry settings for external beam radiotherapy, side effect predictions, organ and/or tumor segmentation, machine therapy attributes, dosage administration attributes (e.g., dosage amount), treatment frequency, treatment timing, etc. The analytics server 110a may provide calibrated predictions for dose distribution for a patient. The predicted values may be used to evaluate the radiation parameters and/or to visualize the dose distribution as depicted in FIGS. 5-6. Additionally or alternatively, the predicted dose distribution values can be ingested by the plan optimizer to iteratively improve the patient's treatment plan.

The analytics server 110a may host a website accessible to users operating any of the electronic devices described herein (e.g., end users), where the content presented via the various webpages may be controlled based upon each particular user's role or viewing permissions. The analytics server 110a may be any computing device comprising a processor and non-transitory machine-readable storage capable of executing the various tasks and processes described herein. Non-limiting examples of such computing devices may include workstation computers, laptop computers, server computers, and the like. While the system 100 includes a single analytics server 110a, the analytics server 110a may include any number of computing devices operating in a distributed computing environment, such as a cloud environment.

The analytics server 110a may execute software applications configured to display the electronic platform (e.g., host a website), which may generate and serve various webpages to each electronic data source 120 and/or end-user devices 140. Different users may use the website to view and/or interact with the predicted results.

The analytics server 110a may be configured to require user authentication based upon a set of user authorization credentials (e.g., username, password, biometrics, cryptographic certificate, and the like). The analytics server 110a may access the system database 110b configured to store user credentials, which the analytics server 110a may be configured to reference in order to determine whether a set of entered credentials (purportedly authenticating the user) match an appropriate set of credentials that identify and authenticate the user.

The analytics server 110a may also store data associated with each user operating one or more electronic data sources 120 and/or end-user devices 140. The analytics server 110a may use the data to weigh interactions while training various AI models 111 accordingly. For instance, the analytics server 110a may indicate that a user is a medical professional whose inputs may be monitored and used to train the machine-learning or other computer models 111 described herein.

The analytics server 110a may generate a user interface (e.g., host or present a webpage) that presents information based upon a particular user's role within the system 100. In such implementations, the user's role may be defined by data fields and input fields in user records stored in the system database 110b. The analytics server 110a may authenticate the user and may identify the user's role by executing an access directory protocol (e.g. LDAP). The analytics server 110*a* may generate webpage content that is customized according to the user's role defined by the user record in the system database 110*b*.

The analytics server 110*a* may receive RTTP data (e.g., patient and treatment data for previously implemented treatments) from a user (medical professional) or retrieve such data from a data repository, analyze the data, and display the results on the electronic platform. For instance, in a non-limiting example, the analytics server 110*a* may query and retrieve medical images from the database 120*d* and combine the medical images with treatment data received from a physician operating the physician device 120*b*. The analytics server 110*a* may then execute various models 111 (stored within the analytics server 110*a* or the system database 110*b*) to analyze the retrieved data. The analytics server 110*a* then displays the results via the electronic platform on the administrator computing device 150, the electronic physician device 120*b*, and/or the end-user devices 140.

The electronic data sources 120 may represent various electronic data sources that contain, retrieve, and/or input data associated with patients and their treatment (e.g., patient data, treatment plans, and radiation parameters). For instance, the analytics server 110*a* may use the clinic computer 120*a*, physician device 120*b*, server 120*c* (associated with a physician and/or clinic), and database 120*d* (associated with the physician and/or the clinic) to retrieve/receive data associated with a particular patient's treatment plan.

End-user devices 140 may be any computing device comprising a processor and a non-transitory machine-readable storage medium capable of performing the various tasks and processes described herein. Non-limiting examples of an end-user device 140 may be a workstation computer, laptop computer, tablet computer, and server computer. In operation, various users may use end-user devices 140 to access the GUI operationally managed by the analytics server 110*a*. Specifically, the end-user devices 140 may include clinic computer 140*a*, clinic database 140*b*, clinic server 140*c*, a medical device, such as a CT scan machine, radiotherapy machine (e.g., a linear accelerator or a cobalt machine), and the like (140*d*), and a clinic device 140*e*.

The administrator computing device 150 may represent a computing device operated by a system administrator. The administrator computing device 150 may be configured to display data retrieved and/or radiation parameters generated by the analytics server 110*a* (e.g., various analytic metrics and/or field geometry) where the system administrator can monitor various models 111 utilized by the analytics server 110*a*, electronic data sources 120, and/or end-user devices 140; review feedback; and/or facilitate training or calibration of the neural networks that are maintained by the analytic server 110*a*.

In operation, a physician may access an application executing on the physician device 120*b* and input patient data and the patient's treatment data (e.g., patient information, patient diagnosis, radiation therapy radiation requirements and thresholds, hot spot and cold spot thresholds, etc.). The analytics server 110*a* may then use a patient identifier to query patient data (e.g., patient anatomy and/or medical images) from the electronic data sources 120. The analytics server 110*a* may then utilize the systems and methods described herein to generate an optimized treatment plan and/or dose distribution for the patient and display the results onto the physician device 120*b*, clinic computer 140*a*, and/or the medical device 140*d* (e.g., a display screen of the radiotherapy machine).

The analytics server 110*a* may be in communication (real-time or near real-time) with the medical device 140*d*, such that a server/computer hosting the medical device 140*d* can adjust the medical device 140*d* based on the radiation parameters generated by the analytics server 110*a*. For instance, the radiotherapy machine may adjust the gantry and couch based on angles and other attributes/parameters determined by the analytics server 110*a*. The analytics server 110*a* may transmit instructions to the radiotherapy machines indicating any number or type of radiation parameters (e.g., field geometry settings) to facilitate such adjustments.

The analytics server 110*a* may store AI models 111 (e.g., neural networks, random forest, support vector machines, etc.) that are trained to predict dose distribution attributes to treat patients at radiotherapy clinics. The analytics server 110*a* may train the AI models 111 using patient data and treatment data associated with patients who were previously treated. For instance, the analytics server 110*a* may receive patient data (e.g., physical attributes and diagnosis) and treatment data (e.g., data corresponding to how the treatment was performed including actual and predicted dose distribution and other radiation parameters that were used during the patient's treatment) from any of the data sources 120.

The analytics server 110*a* may then generate one or more sets of labeled (or sometimes unlabeled) training dataset indicating radiation parameters that were used to treat the patients (and whether they are acceptable or not). The analytics server 110*a* may input the set of labeled training dataset into the stored AI models 111 for training (e.g., supervised, unsupervised, and/or semi-supervised) to train the AI models 111 to predict dose distribution for future treatments. The analytics server 110*a* may continue to feed the training data into the AI models 111 until the AI models 111 are accurate to a desired threshold and store the AI models 111 in a database, such as the database 110*b*. In the illustration of FIG. 1, AI models 111 are shown as being executed by the analytics server 110*a*, but may be stored on analytics server 110*a* or system database 110*b*.

The AI models stored in the database 110*b* may correspond to individual radiotherapy clinics or otherwise different sets of radiotherapy machines (e.g., located at individual radiotherapy clinics, are located in different geographical regions, treat specific types of diseases (e.g., different type of cancers), treat specific genders, etc.). For example, each AI model 111 may be associated with an identifier indicating the radiotherapy clinic, set of radiotherapy machines, or a specific disease for which it is configured to predict dose distribution data.

An operator at a radiotherapy clinic may access an end-user device 140 located at the clinic or access an account associated with the clinic. The operator may provide an input at a user interface that causes the end-user device 140 to transmit a request to access a particular AI model 111 that is associated with the clinic and/or the radiotherapy machines located within the clinic. The request may include an identifier associated with the AI model 111, the clinic, and/or the set of radiotherapy machines that the analytics server 110*a* may use as a key in a look-up table to identify the desired AI model 111. The analytics server 110*a* may receive the request and, in some cases, after authenticating the user, identify the AI model 111 via the identifier. The analytics server 110*a* may transmit the identified AI model 111 to the end-user device 140 or send an alert indicating the end-user device is authorized to access the identified AI model 111. Upon receipt or access to the AI model 111, the end-user device 140 may perform the systems and methods described herein to calibrate the AI model 111 to predict dose distribution data for a patient.

FIG. 2 illustrates a flow diagram of a process executed in an automated dose distribution analysis system, according to an embodiment. The method 200 includes steps 210-220. However, other embodiments may include additional or alternative steps, or may omit one or more steps altogether. The method 200 is described as being executed by an analytics server, such as the analytics server 110a described in FIG. 1). However, one or more steps of method 200 may be executed by any number of computing devices operating in the distributed computing system described in FIG. 1. For instance, one or more computing devices may locally perform part or all of the steps described in FIG. 2 or a cloud device may perform such steps.

At step 210, the analytics server may execute an artificial intelligence model to identify a dose distribution value for an anatomical region of a patient, the artificial intelligence model trained using a training dataset comprising data associated with a plurality of previously implemented radiation therapy treatments on a plurality of previous patients and dose distributions associated with one or more anatomical regions of each previous patient.

The analytics server may access an AI model (e.g., neural network, convolutional neural network, or any other machine-learning model such as random forest or a support vector machine) trained based on a training dataset corresponding to previously treated patients. The analytics server may apply a patient's information (e.g., physical attributes of the patient, treatment attributes of the patient including tumor data and other data produced by a treating physician) to the trained AI model. As a result, the trained AI model may predict new dose distribution values, or identify (evaluate) existing dose distribution values for an anatomical region of the patient. As used herein an anatomical region of the patient may refer to any region of the patient that includes at least one of PTV and/or OAR.

Before accessing or executing the AI model, the analytics server may train the AI model using data associated with previously treated patients to predict dosage distributing for a patient. The AI may be trained by the analytics server or by an external data processing system. Previously treated patients, as used herein, may correspond to patients who were treated by a particular clinic or a set of clinics. The analytics server may generate a training dataset that includes data associated with previously treated patients and their treatment plans (e.g., plan objectives, radiation parameters, or any other data associated with how the treatment was implemented). Additionally or alternatively, the analytics server may augment the training dataset using patient data associated with other clinics.

The analytics server may include various attributes associated with a previously treated patient, such as the patient's physical attributes (e.g., height and weight) and disease attributes (e.g., tumor location) in the training dataset. The analytics server may also collect treatment data associated with the patient's treatments. An example of treatment data associated with previously treated patients may include dose-volume histograms (DVH) of a patient. A DVH, as used herein, may refer to a histogram relating radiation dose to tissue volume in radiation therapy planning. Currently, DVHs are most commonly used as a plan evaluation tool and to compare doses from different plans or to structures. A DVH summarizes (e.g., may visually represent in two or three dimensional graphs) dose distribution of a patient's treatment based on the particular treatment plan. As a result, the AI model may determine a dosage distribution for a treatment that has already been performed. Another example of data associated with a patient's treatment may include clinical goals that correspond to the patient's treatment. As discussed herein, the clinical goals may be used in conjunction with DVHs, such that the training dataset includes a holistic view of each patient's treatment.

The analytics server may use the DVH (for previous patients) to identify a clinical goal and train the AI model accordingly. Generally, a DVH represents a curve (e.g., 2D-curve) that identifies all the dose-volume points from volume=0% to 100%, within each structure (e.g., patient's different organs). However, the initial clinical goals, which are often translated into optimization objectives for plan generation, may be represented by a single point on that DVH curve. In some configurations, those single points may have more relevance in the evaluation stage than other points within a DVH. Clinical goals may be specific to particular treatment sites, dose prescription scheme for a patient, and/or specific importance order for the patient. The analytics server may use the clinical goals to determine what dose distribution values were achieved based on the clinical goals for the patient. Using this information, the analytics server may train the AI model.

Additionally or alternatively, the analytics server may retrieve the clinical goals using different methods. For example, a clinical goal, as defined by the analytics server, can also be a mean-dose value. Therefore, the analytics server may calculate the mean-dose value (using DVH or other methods) and use the mean-dose value as the clinical goal. In other examples, the clinical goal may be other biologically relevant calculation, like Generalized Equivalent Dose.

In addition to or alternative to using DVHs, the analytics server may utilize any dose distribution indicator associated with previous patients to train the AI model. Therefore, training is not limited to DVHs. The analytics server may retrieve any dose distribution from a data repository where the dose distribution indicates how dosage was allocated within a particular anatomic region of the patient. Using this dose distribution and in light of the plan objectives and clinical goals, the analytics server may use various training techniques to train the AI model. For supervised training methods, the analytics server may use labeling information, provided by a clinical expert, to train the AI model.

When analyzing DVHs, the analytics server may also account for their corresponding clinical goals and plan objectives. These additional information may provide additional context around the dose distribution for a patient's anatomical region (e.g., structures). For instance, two different patients may have received treatments and may have very similar DVHs. However, because each patient may have a different clinical goal and plan objectives (because each patient's disease requires different distributions and may require different thresholds), one patient's DVH may violate that patient's unique clinical plans. Therefore, the analytics server may train the AI model using contextual data around each DVH.

As described herein, the AI model may be trained to predict dose for a patient including hot and cold spots. Additionally or alternatively, the analytics server may train AI model to recognize dose patterns from given dose distribution based on the training data. For instance, the analytics server may identify hidden patterns that are unrecognizable using conventional methods (e.g., manual methods or computer-based methods). The analytics server may then augment this recognition with analyzing various other attributes, such as patient attributes and/or clinical goals and plan objectives.

The analytics server may also include any medical images of the patient who was previously treated within the training dataset. For instance, the analytics server may retrieve medical images produced before, during, or after the patient's treatment (e.g., computed tomography (CT) images). The training dataset may also include treatment objectives (also referred to herein as the plan objective) associated with the previously treated patients. Treatment objective of radiotherapy treatment planning may refer to various predetermined rules and thresholds implemented by a physician or a clinician. Following the treatment objectives may be necessary to obtain an optimal balance between delivering a high dose of treatment to PTV and a low dose to intervening tissues, such as OARs. Therefore, the objectives provide thresholds and rules that may dictate a patient's treatment. An example of a threshold included within the objective may be dosage thresholds. For instance, a treating physician may indicate that a maximum or minimum dosage that must be received by PTV and/or OAR.

The objectives may also include various rules and thresholds to identify and avoid hot spots and/or cold spots. As used herein a hot spot refers to a segment or portion (e.g., area, spot, voxel, or any other volume) of an anatomical region or structure of a patient that receives radiation dosage that is higher than the boundaries indicated by the objectives. For instance, the objective may indicate that PTV should receive 50 Gy dosage. The objective may also indicate than any structure of portions of a structure that receives more than 110% dosage is a hot spot. Therefore, the objective provides a 10% threshold and indicates that the PTV should not receive more radiation dosage than the predetermined threshold. If the PTV receives more than 55 Gy, the PTV (or the segment of PTV that receives the 55 Gy) is considered a hot spot.

In contrast, a cold spot, as used herein, refers to a portion of the patient's anatomical region that receives less than the prescribed amount. For instance, the objective may indicate that the PTV must receive 50 Gy radiation. The objective may also define a cold spot as receiving less than 90% of the prescribed dosage. Therefore, if the PTV receives less than 45 Gy, the PTV (or the segment of the PTV that receives 45 Gy) is considered a cold spot.

In some configurations, the AI model may also be trained to identify (or predict) various rules and thresholds discussed herein. Specifically, the rules/thresholds for identifying a hot spot or a cold spot (unwanted dose area) can be the result of executing the AI model. For example, in a case where general treatment objectives do not include rules/thresholds regarding healthy tissue dosage, the AI model can be trained to recognize the hot spots and/or cold spots. The AI model may account for manual tweaks performed by the medical professional to further refine its training to identify the rules and thresholds that necessitated the manual tweak. Medical professionals generally perform the manual tweaks to ensure that the dosage distribution is within permitted tolerances and boundaries. Therefore, even though the AI model may not receive an explicit threshold that defines a hot spot or a cold spot, the AI model can interpolate and infer the threshold based on how the medical professional adjusted one or more attributes of the patient's treatment plan.

The training dataset may include treatment data associated with radiotherapy machines that are located across different radiotherapy clinics, that are located in different geographical regions (e.g., different cities, counties, states, etc.), that treat patients with different characteristics (e.g., that have different genders, weights, heights, body shapes, etc.), and/or that treat patients that have different diseases (e.g., patients with different types of cancers). Consequently, the set of patients may include patients with a diverse set of characteristics that can be used to train the AI model to predict radiation parameters for a wide range of people.

The analytics server may generate the training dataset using various filtering protocols to control the training of the AI model. For instance, the training datasets may be filtered such that the training data set corresponds to previously treated patients at a particular clinic and/or previously treated patients with a specific attribute (e.g., a disease type or a treatment modality). Additionally or alternatively, the analytics server may generate a training dataset that specific to a particular patient. For instance, a treating physician may prescribe a series of radiation therapy treatments for a particular patient. As the patient receives his/her radiation therapy, the analytics server may collect data associated with each treatment. The analytics server may then generate a training dataset that is specific to the patient and includes data associated with that particular patient's treatments.

The analytics server may label the training dataset, such that the AI model can differentiate between desirable and undesirable outcomes. Labeling the training dataset may be performed automatically and/or using human intervention. For instance, the analytics server may analyze a treatment plan, DVH, and/or achieved values for clinical goals for a previously treated patient and may identify various hot spots or cold spots (e.g., by comparing the dosage received with the plan objective thresholds). However, in some cases, a mathematical calculation and identification of a hot spot or a cold spot may not indicate a proper label for machine-learning purposes. For instance, any portion of a patient's organ that receives treatment dosage that is more than or less than a predetermined threshold may be designated as a hot spot or a cold spot respectively. However, in some cases, a hot spot and/or cold spot may not be indicative of a planning error. For instance, the cold spot within an OAR may be acceptable because a cold spot indicates that an OAR is receiving less dosage than anticipated. In the context of radiotherapy treatment, an OAR receiving less dosage may be indicative of good planning (e.g., an organ of the patient that is near the patient's tumor is receiving less harmful radiation). In another example, a hot spot that is located within a center of a tumor may be acceptable. Because a hot spot within the PTV may indicate that the tumor is receiving more harmful dosage than anticipated, which may be acceptable. Therefore, existence of a hot spot or a cold spot may not necessarily indicate bad planning.

In another example, whether a cold spot or a hot spot is acceptable may depend on a patient's attributes, such as the particular disease or a location of the patient's tumor. For instance, a hot spot located within a tumor that is located within the patient's head and/or neck region may be acceptable. However, a hot spot having the same attributes may not be acceptable if the tumor is located elsewhere (e.g., prostate cancer). In another example, whether a cold spot or a hot spot is acceptable may depend on OARs located around the PTV (e.g., certain organs are treated as more important than other organs).

To rectify the above described labeling challenges, the analytics server may display various data attributes associated with a patient's previous treatment on an electronic platform where a medical expert can review the data and determine whether a hot spot or cold spot is acceptable.

Using automatic and/or manual labeling, the analytics server may label the training dataset, such that when trained, the train AI model can distinguish between desirable and undesirable hot spots and cold spots.

Generating a treatment plan, and more specifically determining an ideal dose distribution for a patient, may include evaluating a cost function. While the objective is to apply all the dosage to a patient's PTV without applying any dosage to the patient's OAR, this goal may not be realistically possible because certain OARs may always receive residual dosage as the dosage is applied to PTV. Therefore, a treatment planner (whether a human planner, algorithmic planning, or planning using AI modeling techniques) must balance the amount of dosage received by OAR against the importance of the dosage to be applied to the PTV. In some cases, the planner may sacrifice an OAR, such that PTV receives a proper amount of dosage. The planner may minimize the dosage received by a patient's OAR (also referred to herein as the cost) and weigh the amount of dosage received against the dosage received by the patient's PTV. Therefore, in some cases, the analytics server may also allow a human reviewer to identify whether a previous patient's treatment was acceptable, even though the previous patient's treatment included hot spots or cold spots that mathematically indicate an unacceptable or less than desired treatment plan.

After completing the training dataset, the analytics server may train the AI model using various machine-learning methodologies. The analytics server may train the AI model using supervised, semi-supervised, and/or unsupervised training or with a reinforcement learning approach. For example, the AI model may be trained to predict dosage distribution for a patient. To do so, characteristic values of individual patients within the training dataset may be ingested by the AI model with labels indicating the correct predictions for the patients (e.g., examples of acceptable and unacceptable dosage distribution). The AI model may output dose distribution values for individual patients based on their respective characteristics, and the outputs can be compared against the labels. Using back-propagation techniques, the AI model may update its weights and/or parameters based on differences between the expected output (e.g., the ground truth within the training dataset) and the actual outputs (e.g., outputs predicted by the AI model) to better predict future cases (e.g., new patients).

The analytics server may continue this training process until the AI model is sufficiently trained (e.g., accurate above a predetermined threshold). The computer may store the AI model in memory, in some cases upon determining the AI model has been sufficiently trained.

Additionally or alternatively, the analytics server may train the AI model for predicting dose distributing values from patient image contours of the PTV and OARs. As a result, the trained AI model is able to accurately predict dose distribution values for different treatment modalities (e.g., intensity-modulated radiation therapy (IMRT) or volume modulated arc therapy (VMAT)) based on medical images (and other data) of the patients. The analytics server may continue training the AI model until a predetermined threshold has been met. For instance, the analytics server may continue training the AI model and gauge the output predicted by the trained model against true isodose volumes of the prescription dose (e.g., ground truth). The analytics server may generate a Dice coefficient when comparing the predicted results against the ground truth and may continue training the AI model until the Dice coefficient has reached a predetermined level.

The AI model may be a multi-layered series of neural networks arranged in a hierarchical manner. When trained, the AI model may execute contour-to-dose mapping protocols to predict dosage distribution values. The AI model may ingest medical images and analyze said images to connect the center of a tumor to the edge of the body for all of the patients within the training dataset. The AI model may perform various preprocessing protocols to de-noise the medical images before analyzing them. For instance, AI model may utilize organ segmentation and contouring to detect various anomalies in the medical images that could potentially hinder the training process. Non-limiting examples of these anomalies may include dental fillings, artificial hips, pace makers, fiducial markers, and other objects.

In some configurations, a planner may draw artificial structures, which do not correspond to any anatomical structure of the patient. Drawing the artificial structure is common practice in situations where the planner attempts to manually guide and tweak the optimizer behavior. This manual drawing of artificial structures may lead to a deteriorated plan quality in an automatic optimization workflow, where the user has little, if any, control on the optimization flow. When faced with use cases where the planner has manually adjusted a structure, the analytics server may detect and revise/remove the non-anatomical structures from the optimizer's input (or the training dataset). Also, in a similar fashion, if an anatomical structure deviates too much, with respect to some predetermined threshold, from the expected structure position (e.g., shape or size).

As used herein, fiducial marker refers to a method of imaging guidance where a technician places small metal objects called fiducial markers in or near a tumor in preparation for radiation therapy. Therefore, the fiducial the markers help pinpoint the tumor's location with greater accuracy and allow the treatment team to deliver the maximum radiation dose to the tumor while sparing healthy tissue. While fiducial markers are helpful to identify tumors for medical professionals, their image may hinder the training process because a metal object may inappropriately interfere with the AI model's analysis of the medical image. As a result, the analytics server may revise/remove these images from the training dataset. Alternatively, the analytics server may identify these anomalies and may crop a segment of the medical image that includes these anomalies as a part of pre-processing the training dataset.

The AI model may ingest all the data within the training dataset to identify hidden patterns and connections between data points. To prevent the AI model from over-fitting, the analytics server may utilize various dropout regularization protocols. In an example, the dropout regulation may be represented by the following formula:

$$\text{Dropout}_{rate} = \text{Rate}_{max} \times \left(\frac{\text{Current Number of Filters}}{\text{Maximum number of filters}}\right)^{1/n}$$

The choice for the dropout parameters may be iteratively calculated using empirical data, until the gap between the validation loss and training loss does not tend to increase during training. To assess the overall performance of the AI model, the analytics server may select a set of patients (e.g., test set). The analytics server may then perform a cross validation procedure on the remaining patients. The analytics server may compare the predicted values with true and actual values within the training dataset (e.g., previous treatment of one or more patients). For instance, the analytics server may generate a value representing differences (actual vs. predicted) for the PTV and OARs for the test patient cases. Using this value, the analytics server may gauge how well the AI model is trained.

The analytics server may train the AI model such that the AI model is customized to predict values associated with the corresponding training dataset. For instance, if the analytics server trains an AI model using a training data set specific to a patient, the predicted result may be tailored for that patient. In another example, the analytics server may train the AI model, such that the AI model is trained for a specific type of disease (e.g., prostate cancer).

Upon completion of training, the AI model is ready to predict dosage data for patients. The analytics server may access the trained AI model via the cloud or by retrieving or receiving the AI model from a local data repository. For example, the analytics server may transmit a password or token to a device storing the AI model in the cloud to access the AI model. In another example, the analytics server may receive or retrieve the AI model either automatically responsive to the AI model being sufficiently trained or responsive to a GET request from the analytics server.

The analytics server may execute the trained AI model using a new set of data comprising characteristic values of a patients receiving treatment to generate a predicted dosage distribution. The analytics server may execute the AI model by sequentially feeding data associated with the patient. The analytics server (or the AI model itself) may generate a vector comprising values of the characteristics of the patient (e.g., height, weight, gender, tumor size, tumor location, age, prescribed dosage, body mass index, image data of targets and organs, etc.) and input the vector into the AI model. The AI model may ingest the vector, analyze the underlying data, and output various predictions based on the weights and parameters the AI model has acquired during training.

The analytics server may receive values of characteristics of the patient and/or the radiation parameters from a user (e.g., a clinician, doctor, or the patient themselves) via a user interface and generate a feature vector that includes the values. Additionally or alternatively, the analytics server may retrieve values of characteristics of the patient from storage to include in the feature vector responsive to receiving an identifier of the patient. The analytics server may input the feature vector into the AI model and obtain an output from the AI model.

The analytics server may receive the characteristics for the patient based on a patient identifier that is provided via a user interface of the electronic platform. For example, a clinician may input the name of the patient into the user interface via an end-user device and the end-user device may transmit the name to the analytics server. The analytics server may use the patient's name to query a database that includes patient information and retrieve information about the patient such as the patient's electronic health data records. For instance, the analytics server may query the database for data associated with the patient's anatomy, such as physical data (e.g., height, weight, and/or body mass index) and/or other health-related data (e.g., blood pressure or other data relevant to the patient receiving radiation therapy treatment) and/or geometrical data. The analytics server may also retrieve data associated with current and/or previous medical treatments received by the patient (e.g., data associated with the patient's previous surgeries).

If necessary, the analytics server may also analyze the patient's medical data records to identify the needed patient characteristics. For instance, the analytics server may query a database to identify the patient's body mass index (BMI). However, because many medical records are not digitized, the data processing system may not receive the patient's BMI value using simple query techniques. As a result, the analytics server may retrieve the patient's electronic health data and may execute one or more analytical protocols (e.g., natural language processing) to identify the patient's body mass index. In another example, if the analytics server does not receive tumor data (e.g., end-points) the data analytics server may execute various image recognition protocols and identify the tumor data. The analytics server may also use these methods while preparing or pre-processing the training dataset.

The analytics server may receive additional data from one or more medical professionals. For instance, a treating oncologist may access a platform generated/hosted by the analytics server and may add, remove, or revise data associated with a particular patient, such as patient attributes, radiation parameters, tumor attributes, primary site of treatment, tumor stage, end-point, whether the primary tumor has been extended, and the like. Because tumor staging and the end level attributes are sensitive information that affect patient treatment, this information is typically inputted by the treating oncologist.

The data received by the analytics server (e.g., patient/treatment data) may belong to three categories: numerical, categorical, and visual. Non-limiting examples of numerical values may include patient age, physical attributes, and other attributes that describe the patient. Non-limiting examples of categorical values may include different stages of treatment or disease associated with the patient. Visual data may include medical images representing the patient and his/her treatment regions, such as CT scans or other scans illustrating the patient's tumor.

Another example of a patient characteristic may include specific tumor locations. More specifically, this data may indicate the primary tumor location with respect to the patient's centerline. This data may be inputted by the treating oncologist or may be analyzed using various image recognition or segmentation methods executed on the patient's medical images. This information can also be predicted using the machine-learning model if it is not inputted by the treating oncologist (or otherwise received by the data processing system). Another patient attribute may indicate whether and how close the tumor is to other non-diseased organs (also known as organ at risk or OAR). For instance, a tumor to be eradicated may be millimeters away from another organ. This information may change field geometry, as other organs must be avoided.

The analytics server may also receive plan objectives associated with the patient's treatment. For instance, the analytics server may receive dosages that need to be administered to the PTV. The treatment data may also include various tolerances and thresholds. The thresholds may include a dosage threshold indicating hot and cold spots. As used herein, a hot spot is defined as a volume outside the PTV which receives a dose larger than 100% (or any other threshold) of the specified PTV dose. In contrast, a cold spot refers to an area (e.g., a segment of the patient's PTV or OAR) in which the received dosage is less than a threshold (e.g., less than 70%).

The analytics server may apply the patient's data and plan objectives to the trained AI model. Using the medical images of the patient as well as the identified PTV and the OARs, the AI model may predict a value indicative of a dosage received by the PTV and/or OARs (e.g., different segments or voxels of the PTV or OARs). For instance, the AI model may predict a dosage value received by segments within the patient's anatomical region (e.g., different segments of the patient's OAR or PTV). For instance, the AI model may predict a Gy value for a patient's anatomic region that includes PTV.

As will be described herein, the predicted valued generated by the AI model may be used in various ways to further analyze, evaluate, and/or optimize the patient's treatment plan. In an example, the values outputted by the AI model may be displayed on a graphical user interface. In another example, the AI model's output may be ingested by another software application (e.g., plan optimizer). In yet another example, the AI model may be used to evaluate a treatment plan generated by another software solution (e.g., plan optimizer). Even though these examples are presented herein individually, a skilled artisan will appreciate that the analytics server may perform any combination of above-described examples. For instance, the analytics server may visualize the AI model's predictions and may transmit the predictions to another software solution to optimize the patient's treatment plan.

In addition to predicting dosage amounts discussed herein, the trained AI model may also predict a confidence score associated with the dosage distribution values and/or the treatment plan. The confidence score may correspond to a robustness value of the dose distribution predicted by the AI model. For example, the analytics server may analyze a pre-existing treatment plan using the methods described herein (e.g., by allowing the trained AI model to ingest the plan and determining whether the plan complies with various clinical goals and plan objectives). The AI model may determine that the dose distribution fulfills all goals and objectives of the planner. However, the AI model may also determine that a change in the patient's position (e.g., patient positioning or internal movement of organs) may cause the treatment plan to deviate from the clinical goals and plan objectives. As a result, the AI model may determine that the treatment plan, while acceptable, is not a robust plan. Therefore, the robustness value represents a likelihood of the treatment plan deviating from the clinical goals and plan objectives when an attribute (e.g., patient positioning) changes.

In a non-limiting example, two treatment plans are analyzed by the AI model. The AI model indicates that both treatment plans comply with various rules and thresholds discussed herein (e.g., the plans do not produce hot spots and/or cold spots). However, the AI model generates a confidence value that is significantly lower for the first treatment plan. This indicates that the first treatment plan is more likely to violate one or more rules and thresholds discussed herein (e.g., produce hot spots or cold spots) when one or more factors (e.g., position of the patient while receiving treatment) change.

At step 220, the analytics server may display a heat map having a set of segments where each segment corresponds to a first coordinate and a second coordinate of the anatomical region of the patient, wherein a visual attribute of each segment corresponds to a calculated dose distribution value, wherein at least one segment corresponding to a hot spot exceeding a first threshold or a cold spot below a second threshold is visually distinct from other segments within the heat map.

Referring now to FIGS. 5 and 6, non-limiting examples of visualizing dosage distribution predicted by the AI model are illustrated. Specifically, FIG. 5 illustrates four different examples of dose distribution visualizations predicted by the AI model (e.g., charts 510-540). Each chart represents a heat map of dose distributions within a patient's anatomical region, which is display on a user interface 500, 600, such as a webpage, which may show one or more charts having heat map distributions. In one configuration, a processor of the analytics server presents these charts for display on the user interface.

Chart 510 illustrates different segments within a patient's anatomical region. Specifically, the X-axis and Y-axis within the charts 510-540 represent distances within an anatomical region of the patient. These distances can be used to identify dose distributions within a segment of the patient's anatomical region. For instance, segment 514 visually indicates a value of dosage predicted to be received within a region of the patient's anatomical region that corresponds to distances indicated by segment 514's X and Y-axis coordinates (9-10 on X-axis and 23-24 on Y-axis).

The analytics server may assign a color to each segment within each chart where the color indicates a value of the dosage predicted by the AI model. The analytics server may determine a color based on a coloring scheme where each color and/or shade represents a dosage value predicted by the AI model. In some embodiments, as depicted in FIG. 5, a brighter color may represent a higher dosage. Therefore, as depicted, the AI model predicts that segment 516 receives a higher dose than segment 514. Moreover, the AI model predicts that segment 514 receives a higher dosage than segment 518. Even though the illustrated heat maps use different colors (different shades) to distinguish between different predicted dosage values, the analytics server may use any visual scheme (e.g., coloring scheme) to differentiate between different predicted values, such as by revising any visual attributes (e.g., hatch patterns).

Using the depicted heat maps, a user may quickly and easily identify a large concentration of predicted dosage values. For instance, the segment 520 may indicate a portion of (or all of) the PTV that receives the highest dosage. This may indicate that the segment 520 corresponds to the tumor that is located within the patient's organ. The analytics server may also indicate the existence of a hot spot within the illustrated heat maps. For instance, the analytics server may display the hot spot 512 indicating the location of a hot spot. Charts 520-540 are similar heat maps that visually convey dosage distribution values predicted by the AI model. The charts 520-540 may also visually indicate identify hot spots (e.g., hot spot 522, 532, and 542).

Using the heat maps depicted and described in FIG. 5, a user may easily determine whether a hot spot is acceptable. For instance, as described above, the hot spot 512 is predicted to be within the segment 520, which corresponds to the PTV. Therefore, in certain treatments, existence of a hot spot within the PTV may be acceptable. Therefore, even though the AI model predicts a hot spot, a human reviewer viewing the chart 510 may review and designate the hot spot 512 as acceptable. In contrast, the hot spot 522 and 532 are predicted to be outside PTV's 524 or 534. Therefore, a human reviewer may quickly identify that these hot spots may be violating one or more plan objectives. Moreover, the hot spot 542 is predicted to be located very close to the PTV 534. As a result, the human reviewer viewing the chart 540 may determine to further analyze dose distribution for the patient corresponding to the chart 540.

Referring now to FIG. 6, charts 610-640 depict non-limiting examples of dosage distribution values predicted by the AI model for a patient's anatomical region. The charts 610-640 follow a similar format (coordinates) and coloring scheme as described in FIG. 5. While the charts depicted in FIG. 5 illustrated hot spots, charts 610-640 identify cold spots. Specifically, the analytics server illustrates cold spots 612, 622, 632, and 642. A human reviewer viewing charts 610-640 can easily and quickly identify these cold spots and determine whether the predicted cold spots are acceptable. Specifically, cold spots 612, 622, and 632 are predicted to occur within each patient's PTV. Cold spots are generally unacceptable when they occur within a PTV. Therefore, a human reviewer may determine that cold spots 612, 622, and 632 are unacceptable. In contrast, the cold spot 642 is predicted to occur on the edge of the PTV. This may indicate that the cold spot is predicted to occur within the patient's OAR, which is generally acceptable.

As described herein, the analytics server may display the charts depicted in FIG. 5-6 to visually illustrate the values predicted by the AI model. The charts illustrated in FIGS. 5-6 can be customized, such that they each display predicted values for a certain anatomical region of the patient. The end user may customize the X-axis and Y-axis, such that the analytics server can illustrate a different anatomical region of the patient and/or change the granularity of the segments. Furthermore, the coloring scheme of the heat maps can be customized by each end user.

The analytics server may also display an input field where the human reviewer (viewing the GUIs described in FIGS. 5-6) can accept, deny, or revise the treatment plan. For instance, the human reviewer (medical professional) may designate a hot spot or a cold spot as acceptable. In contrast, the human reviewer may use the input field to indicate that the patient's treatment plan is not acceptable and instruct the plan optimizer to generate a new plan.

Additionally or alternatively, the output generated by the AI model may be ingested by a different software solution (e.g., plan optimizer). The plan optimizer may use the data predicted by the AI model to generate an optimal treatment plan for the patient. The treatment plan may include various radiation parameters to be used during the radiotherapy treatment. These radiation parameters may include, for example, the type, the angle, the radiation intensity and/or the shape of each radiation beam. In determining these parameters, the plan optimizer attempts to achieve a radiation dose distribution to be delivered to the patient that meets predefined criteria, e.g., set by the plan objectives. Such criteria usually include predefined radiation dose thresholds or ranges for the PTV and the OARs to be met.

To optimize the radiation parameters in a way to meet the predefined criteria of the plan objectives, the treatment planner usually runs a plurality of simulations with various radiation parameters, and selects a final set of radiation parameters to be used based on the simulation results. This process usually involves iteratively revising the radiation parameters after each simulation. Such approach may be time consuming, tedious, and may not provide optimal results. Optimization of the radiation treatment trajectory or path leads to improvement of dosimetric quality of a treatment plan. Specifically, the goal of the optimization is to minimize (or maintain below a corresponding predefined upper bound value) the amount of radiation dose for OARs while maximizing (or maintaining above a corresponding predefined lower bound value) the radiation dose for the PTV. In such a case, the radiotherapy designed according to the optimized radiation treatment trajectory can lead to killing the cancerous cells without damaging or harming critical organs or OARs. Trajectory optimization methods based on manual selection and prioritization of critical organs make the task of treatment planners difficult and time consuming for users, require a trial and error procedure where the outcome usually depends on the experience and skill of the treatment planner.

To improve the plan optimization process, the analytics server may transmit the values predicted by the AI model to the plan optimizer. As a result, the plan optimizer may generate a suggested treatment plan and then use the predicted dosage to iteratively revise the suggested treatment plan until the treatment plan is optimized.

Referring now to FIG. 3, a non-limiting visual example of a workflow utilizing the methods and systems described herein is illustrated. In this non-limiting example 300, the analytics server provides prediction data to a plan optimizer 330 to generate a suggested treatment plan that is optimized for a patient. The analytics server may first collect patient data 310. The patient data may include patient anatomy data 310*a*, user inputs 310*b* (received via a user interface from treating oncologist, such as tumor data, PTV identification and the like), and rules 310*c* for the patient's treatment (e.g., hot spot and cold spot threshold and other plan objectives). The analytics server may train a machine-learning model 320 using previously performed radiation therapy treatments and corresponding patient data. The trained machine-learning model 320 may then identify various weights/parameters to predict a dosage distribution for patients.

The analytics server may receive the patient's RTTP file and extract the needed patient data 310. The analytics server then executes the machine-learning model 320 using the patient data 310, such that the machine-learning model 320 ingests the patient data 310 and predicts dosage distribution for an anatomical region of the patient that includes one or more organs of the patient. For instance, the machine-learning model 320 may determine a predicted dosage distribution for different voxels of the patient's PTV and OAR(s). As described above, the machine-learning model 320 is trained using previously performed treatments and their corresponding patient data, RTTP files, user inputs, and other data associated with the patient's treatment (e.g., clinic rules or special instructions received from the treating physician).

The results generated via the machine-learning model 320 may be ingested by the plan optimizer 330. The plan optimizer 330 may be a treatment planning and/or monitoring software solution. The plan optimizer 330 may analyze various factors associated with the patient and the patient's treatment to generate and optimize a treatment plan for the patient (e.g., field geometry, treatment modality, and radiation parameters needed to treat the patient). One of the factors considered by the plan optimizer 330 may be dosage distributions predicted by the machine-learning model 320. While the plan optimizer 330 may consider dosage distribution as a factor, the plan optimizer 330 may weigh the dosage distribution differently than other factors considered to generate the patient's treatment plan. For instance, the treatment plan generated by the plan optimizer 330 may not be dictated by the dose distribution predicted by the machine-learning model 320. The plan optimizer 330 may utilize various cost function analysis protocols where the dosage distribution is evaluated in light of the other (sometimes more important) factors. In some cases, other factors may be prioritized over the dosage distribution.

The plan optimizer 330 may iteratively revise the patient's treatment plan where the plan optimizer 330 iteratively revises different attributes of the patient's treatment plan (e.g., field geometry). With each iteration, the plan optimizer 330 may transmit new treatment plan data back to the machine-learning model 330 whereby the machine-learning model 330 can recalculate/re-predict new dose distribution data based on the revised treatment data generated by the plan optimizer (iteration 322). The plan optimizer 330 and the machine-learning model 320 may repeat the iteration 322 until the patient's treatment plan is optimized. When the plan optimizer completes the patient's treatment plan, the plan optimizer 330 may transmit the suggested treatment plan 340 to one or more electronic devices where a user (e.g., clinician) can review the suggested plan. For instance, the suggested treatment plan 340 may be displayed on a computer of a clinic where a radiotherapy technician or a treating oncologist can review the treatment plan.

As described herein, the plan optimizer 330 may utilize various cost functions to determine whether decreasing hot spots and/or cold spots is appropriate. In some embodiments, the plan optimizer may determine that existence of a hot spot and/or a cold spot identified by the machine-learning model 320 cannot be rectified. Therefore, not every hot spot or cold spot may be eliminated. For instance, the plan optimizer 330 may determine that a cold spot within the patient OAR or a hot spot within the patient's PTV is acceptable. In another example, the plan optimizer 330 may determine that a hot spot within the patient's OAR is acceptable (even though not ideal) in the overall treatment of the patient.

Figure 4:
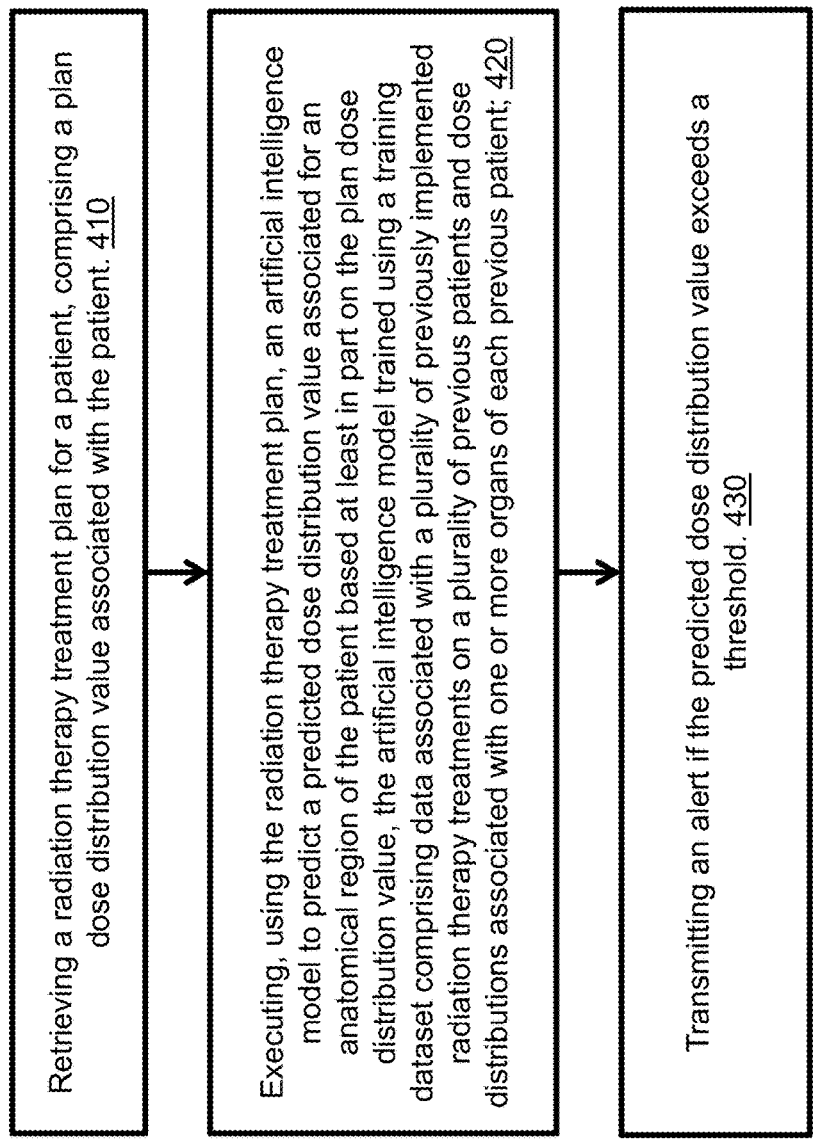
FIG. 4 illustrates a flow diagram of a process executed in an automated dose distribution analysis system, according to an embodiment.

In addition to the embodiments described above, the analytics server may use the trained AI model to independently evaluate a plan generated by the plan optimizer. Referring now to FIG. 4, the method 400 illustrates a flow diagram of a process executed in an automated dose distribution analysis system, according to an embodiment. The method 400 includes steps 410-430. However, other embodiments may include additional or alternative steps, or may omit one or more steps altogether. The method 400 is described as being executed by an analytics server, such as the analytics server 110a described in FIG. 1. However, one or more steps of method 400 may be executed by any number of computing devices operating in the distributed computing system described in FIG. 1. For instance, one or more computing devices may locally perform part or all of the steps described in FIG. 4 or a cloud device may perform such steps.

At step 410, the analytics server may retrieve a radiation therapy treatment plan for a patient comprising a plan dose distribution value associated with the patient. The analytics server may communicate with a software solution configured to generate a treatment plan for a patient, such as the plan optimizer discussed herein. The plan optimizer may execute various analytical protocols to identify and optimize a patient's treatment plan. For instance, the plan optimizer may retrieve patient data (e.g., physical data, disease data, and the like). The plan optimizer may also retrieve plan objectives associated with the patient's treatment. Using the above-mentioned data, the plan optimizer may generate a treatment plan for the patient that includes various treatment and radiation parameters, such as an identification of the treatment modality, field geometry, and the like. The analytics server may then retrieve the suggested treatment from the plan optimizer. The plan generated by the plan optimizer may include various dose distribution values. As will be described below, the analytics server may execute the AI model to evaluate the plan, as generated by the plan optimizer.

At step 420, the analytics server may execute, using the radiation therapy treatment plan, an artificial intelligence model to predict a dose distribution value for an anatomical region of the patient based at least in part of the plan dose distribution values, the artificial intelligence model trained using a training dataset comprising data associated with a plurality of previously implemented radiation therapy treatments on a plurality of previous patients and dose distributions associated with one or more organs of each previous patient.

The analytics server may execute the trained AI model using data received from the plan optimizer (e.g., the patient's treatment plan and dose distribution values received from the plan optimizer). Additionally or alternatively, the AI model may also apply patient data (e.g., plan objectives and the patient's attributes) retrieved by the analytics server. As a result, the AI model may generate a set of predicted dosage distribution values. Because the AI model uses the treatment data generated by the plan optimizer, the AI model may predict the dosage distribution as if the patient is treated in accordance with the treatment plan generated by the plan optimizer. Therefore, the AI model simulates the patient's treatment in accordance with the data generated by the plan optimizer. The analytics server may identify hot spots and cold spots in accordance with the methods described herein.

At step 430, the analytics server may transmit an alert if the predicted dose distribution value exceeds a predetermined threshold. The analytics server may evaluate the hot spots and cold spots predicted by the AI model. Specifically, the analytics server may compare the predicted dose distribution values against the thresholds received via the plan objectives to identify the existence of any hot sports and/or cold spots. If so, the analytics sever may also calculate the location and intensity of the hot spots or cold spots. If the treatment plan generated by the plan optimizer is simulated to generate one or more hot spots or cold spots that violate the plan objectives, the analytics server may transmit an electronic notification to one or more electronic devices associated with the patient's treatment, such as the radiotherapy machine (e.g., display an alert on the radiotherapy machine) and/or a clinician's computer.

The notification may alert the medical professionals involved with the patient's treatment that the treatment plan generated by the plan optimizer is simulated to produce hot spot(s) and/or cold spot(s) that violate the plan objectives. The notification may also include visualization of the predicted hot spot(s) and/or cold spot(s), as depicted in FIGS. 5-6. The medical professional may review the anomalies predicted by the AI model to accept or reject the treatment plan.

In addition to training the AI model as discussed above, the analytics server may use user interactions to further train and re-calibrate the AI model. When an end user performs an activity on the electronic platform that displays the results predicted via the AI model, the analytics server may track and record details of the user's activity. For instance, when a predicted result is displayed on a user's electronic device, the analytics server may monitor the user's electronic device to identify whether the user has interacted with the predicted results by editing, deleting, accepting, or revising the results. The analytics server may also identify a timestamp of each interaction, such that the analytics server records the frequency of modification, duration of revision/correction.

The analytics server may utilize an application programming interface (API) to monitor the user's activities. The analytics server may use an executable file to monitor the user's electronic device. The analytics server may also monitor the electronic platform displayed on an electronic device via a browser extension executing on the electronic device. The analytics server may monitor multiple electronic devices and various applications executing on the electronic devices. The analytics server may communicate with various electronic devices and monitor the communications between the electronic devices and the various servers executing applications on the electronic devices.

Using the systems and methods described herein, the analytics server can have a formalized approach to generate, optimize, and/or evaluate dose distribution in a single automated framework based on various variables, parameters, and settings that depend on the patient and/or the patient's treatment. The systems and methods described herein enable a server or a processor associated with (e.g., located in) a clinic to generate radiation parameters that are optimized for individual patients, replacing the need to depend on a technician or doctor's subjective skills and understanding.

Figure 7:
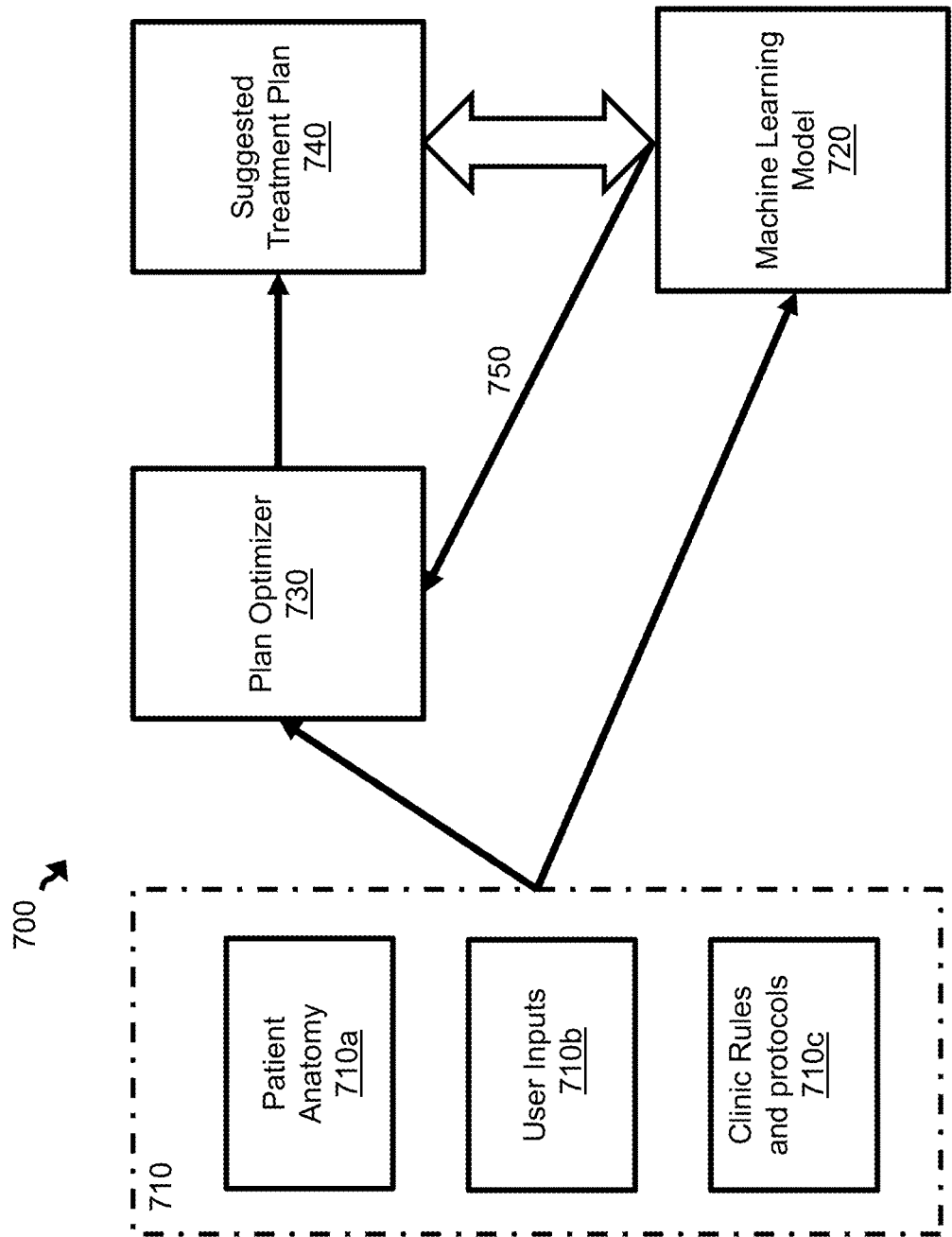
FIG. 7 illustrates a flow diagram of a process executed in an automated dose distribution analysis system, according to an embodiment.

Referring now to FIG. 7, another non-limiting visual example of a workflow utilizing the methods and systems described herein is illustrated. In this non-limiting example 700, the analytics server uses the methods discussed herein to evaluate a plan generated by a plan optimizer 730. In the depicted embodiment, the plan optimizer 730 and a machine-learning model 720 may work independently (as opposed to working together, as depicted in FIG. 4).

The analytics server may first collect patient data 710. As described above, the patient data 710 may include patient anatomy data 710a, user inputs 710b (received from treating oncologist), and rules 710c (plan objectives). The analytics server may train the machine-learning model 720 using previously performed radiation therapy treatments and corresponding patient data. The analytics server may then transmit the patient data to the plan optimizer 730 where the plan optimizer 730 uses various analytical protocols and cost functions to generate a treatment plan for the patient using the patient data 710 (suggested treatment plan 740).

The analytics server may then transmit the patient data and/or the suggested treatment plan 740 to the trained machine-learning model 720. The trained machine-learning model 720 may then use the methods described herein to calculate dose distribution values for different anatomical regions of the patient (e.g., PTV or OARs). Specifically, the trained machine-learning model 720 may identify various weights/parameters to predict a dosage distribution based on the patient data 710 and/or the suggested treatment plan 740. Therefore, the trained machine-learning model 720 simulates dosage distribution for the patient based on the suggested treatment plan 740. As a result, the analytics server can evaluate accuracy and precision of the suggested treatment plan 740 before implementing the plan itself (e.g., simulate dosage distribution before the patient's treatment starts).

The analytics server may then compare the simulated dosage distribution values (generated by the machine-learning model 720) with various thresholds to determine whether the suggested treatment plan 740 produces any hot spots or cold spots. If the analytics server determines that the suggested treatment plan 740 produces dose distribution that is beyond a predetermined tolerable amount, the analytics server may generate a notification and transmit the notification to an electronic device associated with the patient's treatment. For instance, the analytics server may transmit a notification and present an alert to be displayed on a radiotherapy machine and/or a computer associated with the clinic (e.g., clinician's device). The alert may notify a clinician or a radiotherapy technician that the suggested treatment plan 740 creates dosage distribution that is beyond tolerable amounts.

Additionally or alternatively, the trained machine-learning mode 720 (or the analytics server) may transmit the simulated dosage distribution values back to the plan optimizer 730 (step 750). The plan optimizer 730 may then use the simulated values to recalculate a treatment plan for the patient and generated a new suggested treatment plan accordingly. Upon the plan optimizer 730 generating a new suggested treatment plan, the trained machine-learning model 720 may re-evaluate the new suggested treatment plan using the methods described herein. The plan optimizer 730 and the trained machine-learning model 720 may iteratively repeat this process where with each iteration the plan optimizer 730 revises the suggested treatment plan 740 and the trained machine-learning model 720 re-evaluates the revised treatment plan. This iterative process may continue until the trained machine-learning model 720 determines that the suggested treatment plan 740 produces dosage distribution within tolerable thresholds (e.g., plan objectives).

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of this disclosure or the claims.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc., may be passed, forwarded, or transmitted via any suitable means including memory sharing, message passing, token passing, network transmission, etc.

The actual software code or specialized control hardware used to implement these systems and methods is not limiting of the claimed features or this disclosure. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the embodiments described herein and variations thereof. Various modifications to these embodiments will be readily apparent to those skilled in the art, and the principles defined herein may be applied to other embodiments without departing from the spirit or scope of the subject matter disclosed herein. Thus, the present disclosure is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What we claim is:

1. A method comprising:
   retrieving, by a processor, a radiation therapy treatment plan for a patient comprising a plan dose distribution value associated with the patient;
   executing, by the processor using the radiation therapy treatment plan, an artificial intelligence model to predict a predicted dose distribution value for an anatomical region of the patient based at least in part on the plan dose distribution value, the artificial intelligence model trained using a training dataset comprising data associated with a plurality of previously implemented radiation therapy treatments on a plurality of previous patients and dose distributions associated with one or more organs of each previous patient; and
   transmitting, by the processor, a notification when the predicted dose distribution value exceeds a threshold corresponding to a criterion to identify a first region indicating a hot spot or a second region indicating a cold spot.

2. The method of claim 1, wherein the threshold is retrieved from a plan objective associated with the patient.

3. The method of claim 1, wherein the threshold corresponds to at least one dose distribution value within an existing treatment plan generated by a plan optimizer software solution.

4. The method of claim 1, wherein the radiation therapy treatment plan is generated by a plan optimizer application and further comprising:
   transmitting, by the processor, data associated with the at least one dose distribution value predicted by the artificial intelligence model to the plan optimizer application.

5. The method of claim 1, wherein the artificial intelligence model is trained using dose-volume histograms of previous patients and their corresponding first and second thresholds.

6. The method of claim 1, wherein the artificial intelligence model is trained using a set of medical images associated with previous patients.

7. The method of claim 6, wherein the processor revises at least one medical image from the set of medical images that includes a particular object.

8. The method of claim 1, wherein the notification comprises a heat map having a set of segments where each segment corresponds to a first coordinate and a second coordinate of the anatomical region of the patient, wherein a visual attribute of each segment corresponds to a calculated dose distribution value.

9. A computer system comprising:
   a server comprising a processor and a non-transitory computer-readable medium containing instructions that when executed by the processor causes the processor to perform operations comprising:
   retrieve a radiation therapy treatment plan for a patient comprising a plan dose distribution value associated with the patient;
   execute, using the radiation therapy treatment plan, an artificial intelligence model to predict a predicted dose distribution value for an anatomical region of the patient based at least in part on the plan dose distribution value, the artificial intelligence model trained using a training dataset comprising data associated with a plurality of previously implemented radiation therapy treatments on a plurality of previous patients and dose distributions associated with one or more organs of each previous patient; and
   transmit a notification when the predicted dose distribution value exceeds a threshold corresponding to a criterion to identify a first region indicating a hot spot or a second region indicating a cold spot.

10. The computer system of claim 9, wherein the threshold is retrieved from a plan objective associated with the patient.

11. The computer system of claim 9, wherein the threshold corresponds to at least one dose distribution value within an existing treatment plan generated by a plan optimizer software solution.

12. The computer system of claim 9, wherein the radiation therapy treatment plan is generated by a plan optimizer application and the instructions further cause the processor to:
    transmit the at least one dose distribution value predicted by the artificial intelligence model to the plan optimizer application.

13. The computer system of claim 9, wherein the artificial intelligence model is trained using dose-volume histograms of previous patients and their corresponding first and second thresholds.

14. The computer system of claim 9, wherein the artificial intelligence model is trained using a set of medical images associated with previous patients.

15. The computer system of claim 14, wherein the instructions are configured to further cause the processor to revise at least one medical image from the set of medical images that includes a particular object.

16. The computer system of claim 9, wherein the notification comprises a heat map having a set of segments where each segment corresponds to a first coordinate and a second coordinate of the anatomical region of the patient, wherein a visual attribute of each segment corresponds to a calculated dose distribution value.

17. A computer system comprising:
a processor in communication with an artificial intelligence model and an electronic device, the processor configured to:
   retrieve a radiation therapy treatment plan for a patient comprising a plan dose distribution value associated with the patient;
   execute, using the radiation therapy treatment plan, the artificial intelligence model to predict a predicted dose distribution value for an anatomical region of the patient based at least in part on the plan dose distribution value, the artificial intelligence model trained using a training dataset comprising data associated with a plurality of previously implemented radiation therapy treatments on a plurality of previous patients and dose distributions associated with one or more organs of each previous patient; and
   transmit a notification, to the electronic device, when the predicted dose distribution value exceeds a threshold corresponding to a criterion to identify a first region indicating a hot spot or a second region indicating a cold spot.

18. The computer system of claim 17, wherein the threshold is retrieved from a plan objective associated with the patient.

* * * * *